(12) United States Patent
Klima et al.

(10) Patent No.: US 6,543,453 B1
(45) Date of Patent: *Apr. 8, 2003

(54) METHODS OF REFRACTIVE CORRECTION OF THE EYE

(75) Inventors: William L. Klima, Stafford, VA (US); Thomas J. Chambers, Upland, CA (US)

(73) Assignee: ScienceVision L.L.C., Stafford, VA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/306,428

(22) Filed: May 6, 1999

(51) Int. Cl.$^7$ ................................................ A61B 19/00
(52) U.S. Cl. ............................. 128/898; 606/4; 606/27; 606/107; 606/5; 623/4.1; 623/5.11; 623/6.11
(58) Field of Search ........................... 606/4–6, 27, 166, 606/107; 128/899; 607/54; 351/216; 623/4.1, 5.11, 5.12, 6.11, 4–6

(56) References Cited

U.S. PATENT DOCUMENTS

| | | | | |
|---|---|---|---|---|
| 5,403,335 A | * | 4/1995 | Loomas et al. | 606/161 |
| 5,405,384 A | * | 4/1995 | Silvestrini | 623/5 |
| 5,645,582 A | * | 7/1997 | Silvestrini et al. | 623/5 |
| 5,876,439 A | * | 3/1999 | Lee | 623/5 |
| 5,891,131 A | * | 4/1999 | Rajan et al. | 606/5 |
| 6,006,756 A | * | 12/1999 | Shadduck | 128/899 |
| 6,125,294 A | * | 9/2000 | Scholl et al. | 600/407 |

* cited by examiner

Primary Examiner—Linda C. M. Dvorak
Assistant Examiner—Ahmed Farah
(74) Attorney, Agent, or Firm—Law Offices of William L. Klima, P.L.C.

(57) ABSTRACT

A method of changing the shape and/or size of an intracorneal ring in situ. The intracorneal ring can be a lens. Preferably, the intracorneal ring is made of a collagen-based polymer material such as COLLAMER.

14 Claims, 9 Drawing Sheets

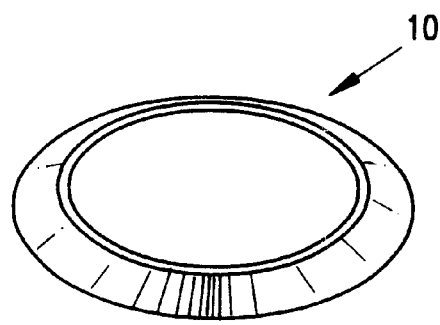
FIG. 1
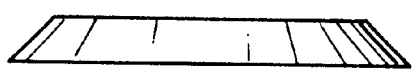
FIG. 2
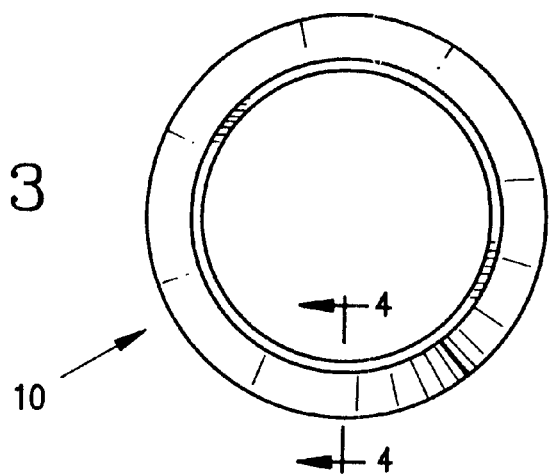
FIG. 3
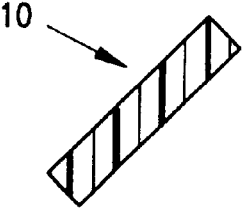 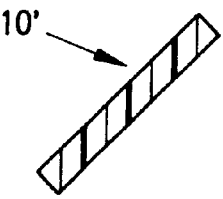 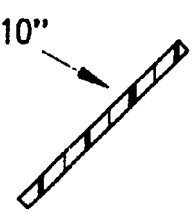
FIG. 4   FIG. 5   FIG. 6

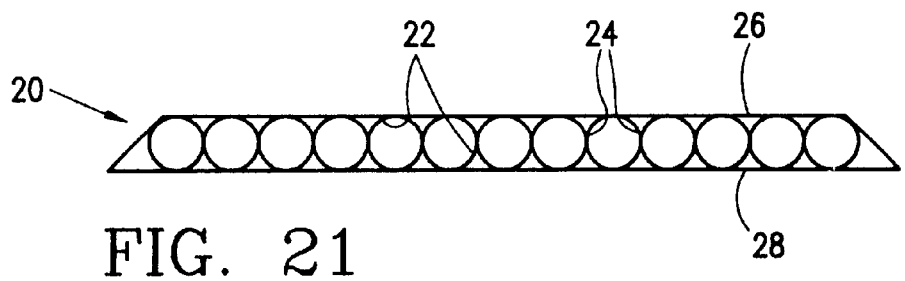
FIG. 21
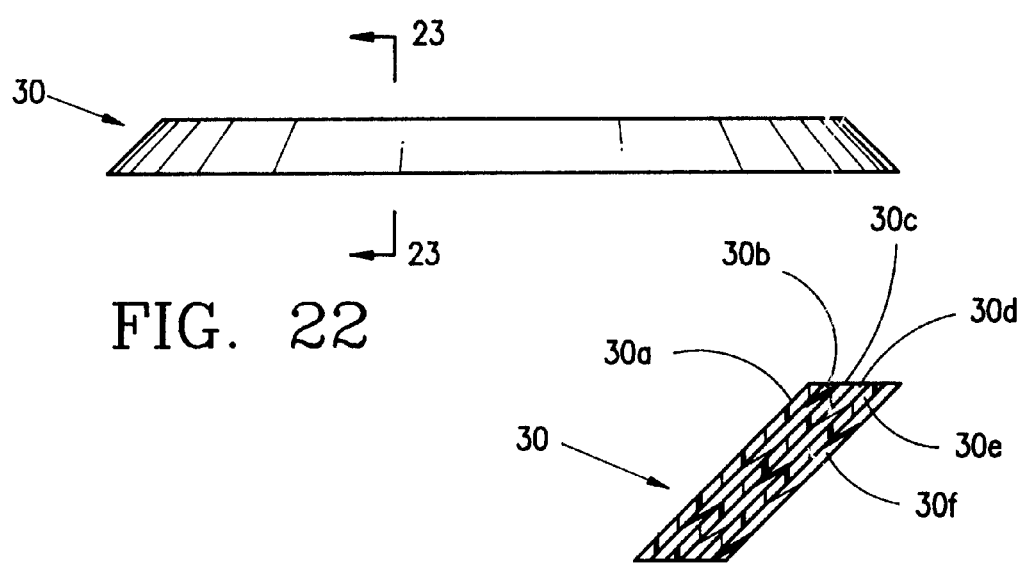
FIG. 22
FIG. 23
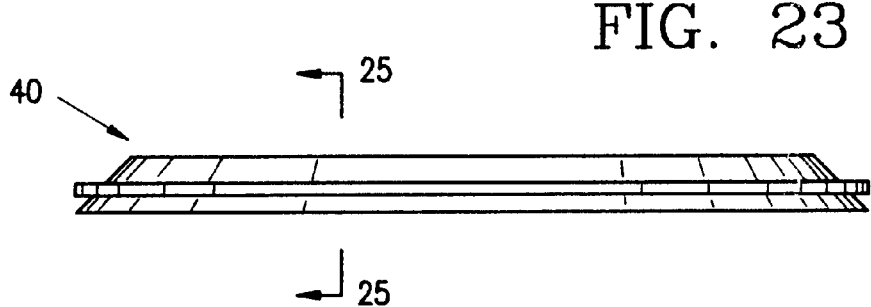
FIG. 24
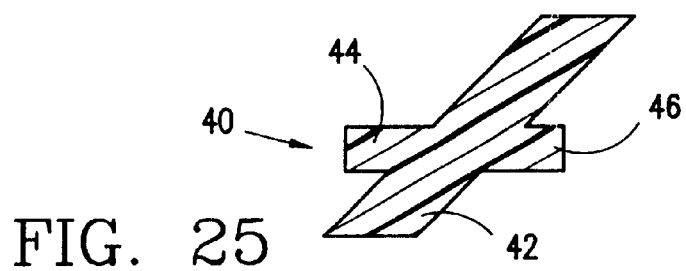
FIG. 25

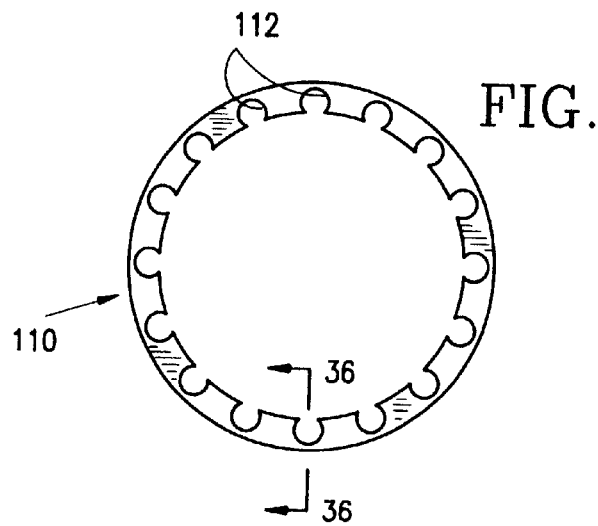
FIG. 35
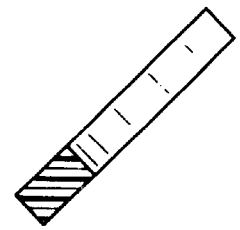
FIG. 36
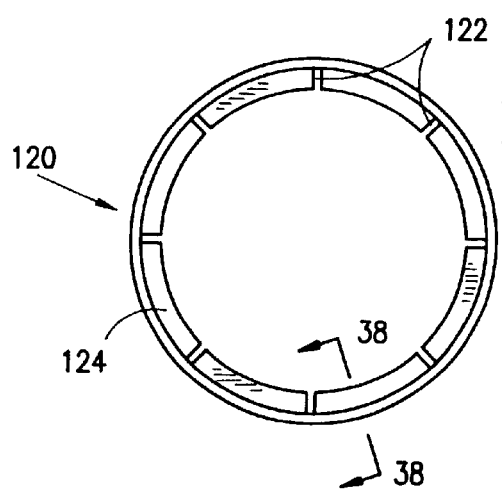
FIG. 37
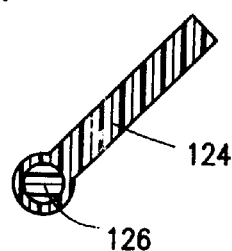
FIG. 38
FIG. 39
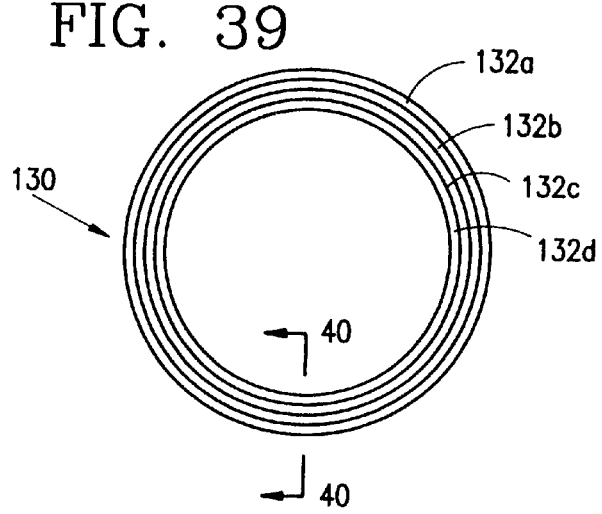
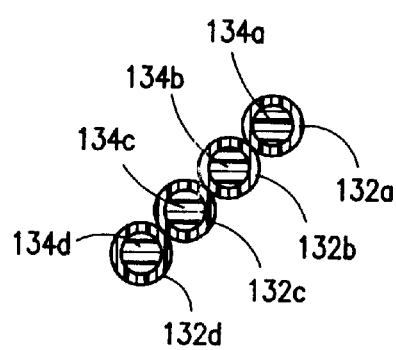
FIG. 40

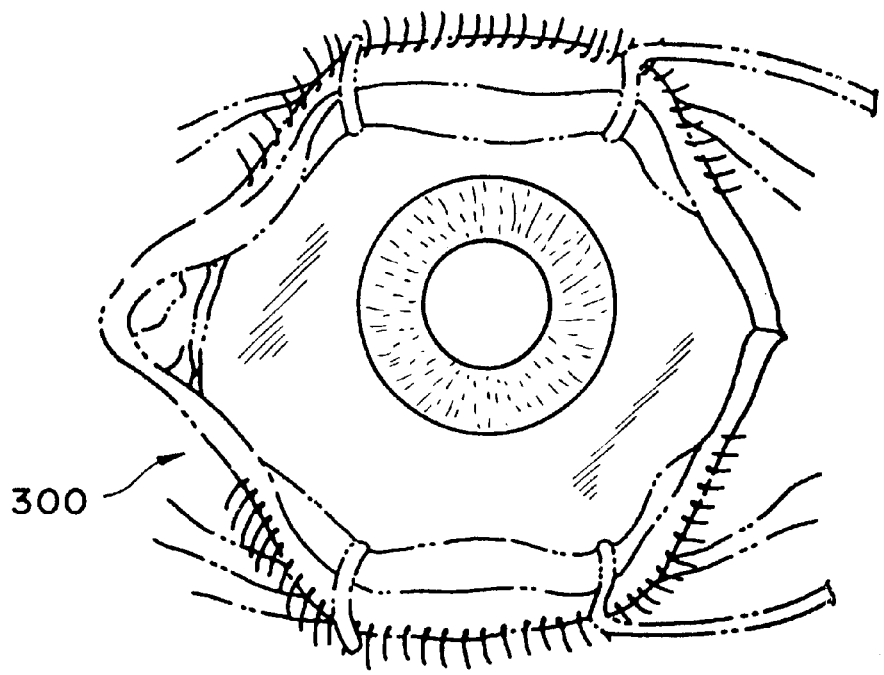
FIG. 54
FIG. 55
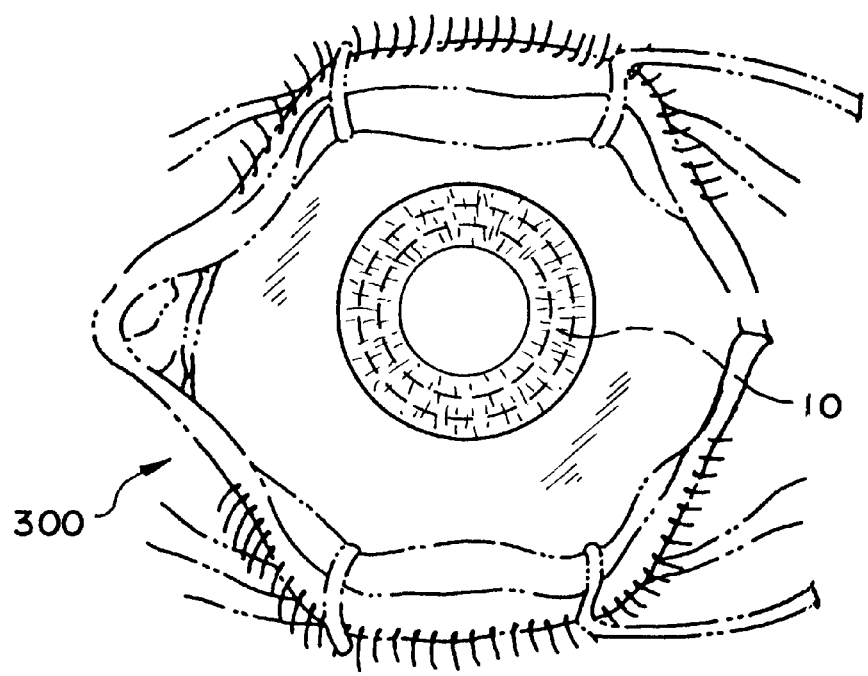

METHODS OF REFRACTIVE CORRECTION OF THE EYE

FIELD OF THE INVENTION

The present invention is directed to refractive correction devices including a phakic intraocular lens and/or intracorneal ring. Further, the present invention is directed to the combination of a phakic intraocular lens and intracorneal ring. The intracorneal ring according to the present invention is preferably adjustable in size, shape and/or configuration. The phakic intraocular lens and intracorneal ring according to the present invention are preferably biocompatible. The present invention is also directed to methods of refractive correction of the eye.

BACKGROUND OF THE INVENTION

The refractive correction of the human eye is a rapidly developing market in the United States and the world. Many patients are interest in getting rid of their conventional eye glasses and/or contact lenses to improve their personal looks and benefit from the numerous conveniences from these refractive correction procedures over wearing conventional eye glasses and/or contact lenses.

The current methods for refractive correction of the eye include LASIK surgery, a procedure for reshaping the cornea with a laser underneath a flap of the cornea, implantation of a phakic intraocular lens (e.g. Implantable Contact Lens (ICL), a phakic refractive lens (prk) manufactured by Staar Surgical AG of Switzerland), implantation of an intracorneal ring (icr) into the stroma of the eye, and other surgical procedures including prk and rk.

Staar Surgical AG of Switzerland has been researching and developing a phakic refractive lens (prl) for implantation in the posterior chamber and located between the iris and natural crystalline lens. The Implantable Contact Lens® brand phakic corrective lens is currently capable of correcting +10 to 18 diopters and −10 to 18 diopters correction. There exists a number of parameters that must be considered for preparing the proper size and prescription of the Implantable Contact Lens® to achieve a high level of visual acuity once implanted in a patient's eye.

The present invention proposes making a substantial correction of vision with the Implantable Contact Lens brand phakic corrective lens, and then possibly following up with one or more additional refractive correction procedures to fine tune the patient's eye for high visual acuity. Specifically, it is possible to over correct or under correct a patients eye with an Implantable Contact Lens brand phakic refractive corrective lens during an operation. Further, due to the effects of healing and/or aging of the patient's eye, it may become necessary to provide an additional subsequent procedure to fine tune a minor refractive correction of the patient's eye to achieve a high level of visual acuity. Thus, after implantation of an Implantable Contact Lens brand phakic refractive lens the patient's eye may be treated immediately or later in time with a subsequent procedure such as LASIK and/or implantation of an intracorneal ring.

SUMMARY OF THE INVENTION

An object of the present invention is to provide a refractive correction device in the eye.

A second object of the present invention is to provide multiple refractive correction devices in the eye.

A third object of the present invention is to provide a refractive correction device in combination with a refractive correction procedure in the eye.

A fourth object of the present invention is to provide the combination of a phakic refractive lens and an adjustable intracorneal ring.

A fifth object of the present invention is to provide an adjustable intracorneal ring arranged so that the size, shape, and/or configuration can be changed prior to insertion in the eye.

A sixth object of the present invention is to provide an adjustable intracorneal ring arranged so that the size, shape and/or configuration of the adjustable intracorneal ring can be adjusted after being implanted in the eye.

A seventh object of the present invention is to provide an adjustable intracorneal ring arranged so that the size, shape and/or configuration of the intracorneal ring can be changed after being implanted in the eye by electromagnetic waves such as light, laser, electromagnetic, electromagnestrictive, etc.

An eighth object of the present invention is to provide a method of refractive correction of an eye.

A ninth object of the present invention is to provide a method of refractive correction of the eye including the step of adjusting the size, shape, and/or configuration of an intracorneal ring after being implanted in the eye.

A tenth object of the present invention is to provide a method of refractive correction of an eye including the steps of providing at least two refractive correction devices and/or refractive correction procedures of the eye.

The present invention is to provide for the refractive correction of an eye. The present invention can include refractive correction devices and/or refractive correction procedures. Preferably, the present invention is directed to refractive correction of the eyes with multiple refractive correction devices and/or refractive correction procedures.

A preferred embodiment of the present invention includes providing a phakic refractive lens (e.g. Implantable Contact Lens brand phakic refractive lens) in combination with an intracorneal ring in the eye. Preferably, the refractive correction lens is first implanted and then the intracorneal ring is implanted immediately thereafter. However, the intracorneal ring can be implanted minutes, hours, days, or weeks later. The phakic refractive lens can be a hard lens (e.g. made of polymethyl methacrylate PMMA) or more preferably a deformable phakic refractive lens (e.g. made of a resilient biocompatible material such as a collagen-based polymer (e.g. Collamer), silicone, hydrogel, or other suitable biocompatible polymer or plastic material). The phakic corrective lens can be for correction of power only and/or can be for the correction of power and astigmatism. For example, the phakic correction lens can be a toric phakic correction lens (e.g. toric implantable contact lens and/or prism phakic correction lens). The intracorneal ring can be a single ring, one or more segments of a ring, a composite ring made of different materials or layers of materials, or an adjustable intracorneal ring. A preferred combination is an Implantable Contact Lens brand phakic refractive lens with an adjustable intracorneal ring.

Another preferred embodiment of the present invention is providing a phakic refractive lens with a intracorneal refractive lens ring. The intracorneal refractive lens ring is an intracorneal ring configured to provide refractive properties with or without lens power correction ability. The intracorneal refractive lens ring can be configured to focus light to provide near sight visual acuity, for example, after LASIK surgery which typically decreases near visual acuity of the patient. The bulk opr displace volume of the intracorneal refractive lens ring dictates the extent to which this device will also provide lens power correction of the cornea of the patient. For example, the device can be made very thin so as to have no power correction effect, or it can be increased in thickness to provide some lens power correction. The intracorneal refractive lens ring can be in the configuration of a one-piece ring or can be one or more segments of a ring. The device, for example, can be implanted by first tunneling a circular path between layers of the stroma with a surgical instrument (e.g. treefind), and then the ring or segments can be implanted in the circular tunnel.

A further preferred embodiment of the present invention is to provide the combination of a LASIK correction procedure with an intracorneal ring with or without refractive lens properties. Specifically, the intracorneal ring can be configured to provide bulk in the stroma of the eye to provide lens power correction. Alternatively, the intracorneal ring can be an intracorneal refractive lens ring configured to change the focal point of a portion of the eye with or without bulk to optionally change the lens power of the eye.

An even further preferred embodiment of the present invention is to provide an adjustable intracorneal ring (AICR). The adjustable intracorneal ring can be configured so that the size, shape and/or configuration of the intracorneal ring can be changed after manufacture, but prior to final prescription, adjusted after prescription, adjusted prior to implantation, and/or adjusted after implantation (e.g. in situ). The adjustable intracorneal ring can be configured to be adjusted by mechanical, hydraulic and/or pneumatic means. Alternatively, or in addition, the adjustable intracorneal ring can be adjusted by electromagnetic waves, for example, heat, UV, laser, electromagnetic, electromagnetostrictive, X-ray, or other suitable wavelength of electromagnetic radiation. The use of a laser is particularly preferable for adjustment of the adjustable intracorneal ring once implanted in the eye, since the laser can be adjusted to pinpoint accuracy.

The adjustable intracorneal ring according to the present invention is configured to be adjusted in size, shape and/or configuration. The adjustable intracorneal ring can be made of material that will change in size, shape, and/or configuration when a mechanical, hydraulic, pneumatic and/or electromagnetic radiation is applied to the adjustable intracorneal ring. Alternatively, or in addition, the adjustable intracorneal ring can be configured by design to be adjustable when a mechanical force, hydraulic force, pneumatic force and/or electromagnetic radiation is applied to the adjustable intracorneal ring. For example, the adjustable intracorneal ring can be designed with varying thicknesses or other dimensions, one or more holes, passageways, grooves, edges, layers, cells, matrixes, strata, grain, bubbles, voids, indentations, surface roughening, surface finish, or other physical parameters can be designed to allow the ring to be permanently and/or non-permanently adjusted. The adjustable intracorneal ring according to the present invention can be designed and/or configured to be reversibly adjusted. In another preferred embodiment of the adjustable intracorneal ring according to the present invention, the size of the adjustable intracorneal ring can be increased or decreased. Further, in another embodiment, the direction of movement of portions of the adjustable intracorneal ring can be moved in various directions.

The adjustable intracorneal ring according to the present invention can be adjustable in thickness to vary the amount of bulk, and thus the amount of power correction of the eye. Alternatively, or in addition, the overall shape of the adjustable intracorneal ring can be adjusted to vary the visual axis to adjust for astigmatism of the vision of the particular eye. For example, the ring can be made oval in shape along a particular visual axis to compensate for astigmatism. In addition, an adjustable intracorneal refractive lens ring can be adjustable to change the focal length of a portion of the light entering the eye to change the near visual acuity.

The intracorneal ring according to the present invention is preferably made of a clear translucent material such as polymethylmethacrylate (PMMA), silicone, hydrogel, collagen-based polymer (e.g. Collamer), and other suitable polymers and plastics. Alternatively, the intracorneal ring according to the present invention can be colored. For example, the intracorneal ring can be colored to match the color of the patient's iris. Further, the intracorneal ring according to the present invention can be colored in a specific pattern to match the striations and color of the natural iris of the patients. In addition, the intracorneal ring according to the present invention can be specifically textured (e.g. provided with radial groove striations) in addition to a coloring pattern to closely match with the color pattern and texture pattern of the natural iris of the patient's eye. A computer method of matching the color pattern and texturing pattern of the patient's eye at the exact location where the implant will be placed in the cornea can be developed to carefully match a prescription of the intracorneal ring. Alternatively, the intracorneal ring can be configured to reflect the color pattern and texturing pattern of the patient's natural cornea at a portion adjacent to the location of the intracorneal ring. For example, the intracorneal ring can be tinted and/or provided with at least one reflective surfaces to reflect the coloring pattern and texturing pattern of the patient's eye to a person looking closely at a patient's eye with the implants.

A preferred adjustable intracorneal ring according to the present invention is made from a material having some water content, most preferably a high water content. For example, hydrogels and/or Collamer material can potentially be adjusted in thickness and/or shape and/or configuration by being exposed to a laser. For example, the laser can potentially change the water content and/or confirmation of the polymer strands making up the polymer material. Thus, the size, shape and/or configuration at local points or overall can be changed by treatment with a laser prior to implantation or after implantation (i.e. insitu). For example, an intracorneal ring or ring segments can be adjusted in size, shape and/or configuration to adjust the lens power and/or lens axis to adjust for astigmatism by exposing the implanted Collamer intracorneal ring with a laser insitu to make final corrections of visual power and acuity.

BRIEF DESCRIPTION OF THE DRAWINGS

FIG. 1 is a perspective view of an embodiment of an intracorneal ring according to the present invention.

FIG. 2 is a side elevational view of the intracorneal ring shown in FIG. 1.

FIG. 3 is a top planar view of the intracorneal ring shown in FIG. 1.

FIG. 4 is a transverse cross-sectional view of the intracorneal ring, as indicated in FIG. 3.

FIG. 5 is a transverse cross-section view of another embodiment of an intracorneal ring similar to the embodiment shown in FIGS. 1–4, however, with less thickness.

FIG. 6 is a transverse cross-section view of a further embodiment of an intracorneal ring similar to the embodiment shown in FIGS. 1–4, however, with even less thickness.

FIG. 21 is a side elevational view of another embodiment of an intracorneal ring according to the present invention configured to be adjustable in height in situ.

FIG. 22 is a side elevational view of a further embodiment of an intracorneal ring constructed of multiple layers, and adjustable in thickness in situ.

FIG. 23 is a transverse cross-sectional view of the intracorneal ring, as indicated in FIG. 22.

FIG. 24 is a side elevational view of even a further embodiment of an intracorneal ring provided with a horizontally oriented plate-type haptic portions to dimensional stabilize the intracorneal ring.

FIG. 25 is a transverse cross-sectional view of the intracorneal ring, as indicated in FIG. 24.

FIG. 35 is a top planar view of another embodiment of an intracorneal ring configured to be adjustable in diameter in situ.

FIG. 36 is a transverse cross-sectional view of the intracorneal ring, as indicated in FIG. 35.

FIG. 37 is a top planar view of another embodiment of an intracorneal ring configured to be adjustable in diameter in situ.

FIG. 38 is a transverse cross-sectional view of the intracorneal ring, as indicated in FIG. 37.

FIG. 39 is a top planar view of another embodiment of an intracorneal ring configured to be adjustable in diameter in situ.

FIG. 40 is a transverse cross-sectional view of the intracorneal ring, as indicated in FIG. 39.

FIG. 54 is a front elevational view of an eye prior to implantation of an intracorneal ring.

FIG. 55 is a front elevational view of an eye after implantation of an intracorneal ring according to the present invention.

DETAILED DESCRIPTION OF PREFERRED EMBODIMENTS

Figures 7, 8, 9, 10:
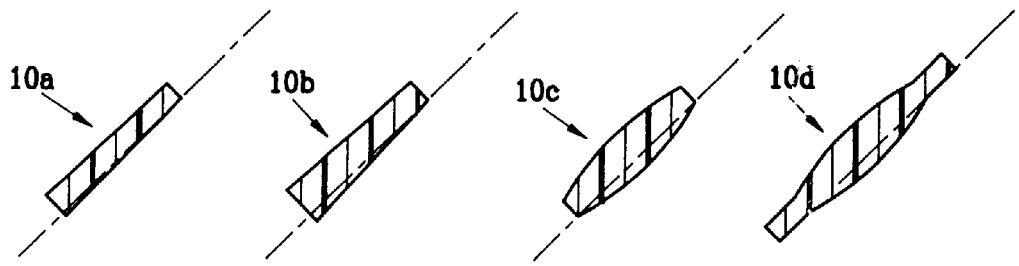
FIG. 7 is a transverse cross-sectional view of another embodiment of an intracorneal ring similar to the embodiment shown in FIGS. 1–4, however, with a prism lens cross-sectional shape.
FIG. 8 is a transverse cross-sectional view of another embodiment of an intracorneal ring similar to the embodiment shown in FIGS. 1–4, however, with a prism lens cross-sectional shape.
FIG. 9 is a transverse cross-sectional view of another embodiment of an intracorneal ring similar to the embodiment shown in FIGS. 1–4, however, with a bi-convex lens cross-sectional shape.
FIG. 10 is a transverse cross-sectional view of another embodiment of an intracorneal ring similar to the embodiment shown in FIGS. 1–4, however, with a plate type biconvex lens cross-sectional shape.
Figures 11, 12, 13, 14:
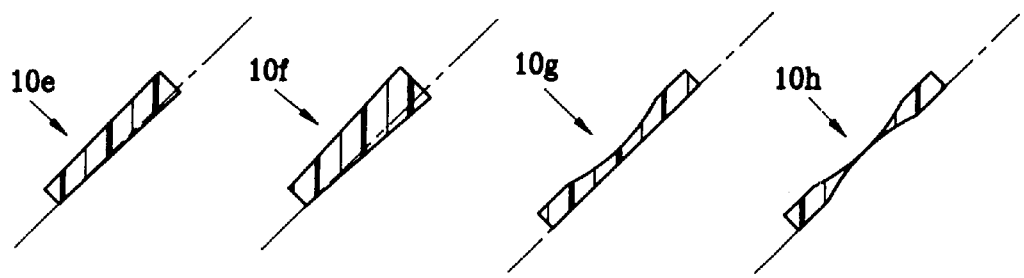
FIG. 11 is a transverse cross-sectional view of another embodiment of an intracorneal ring similar to the embodiment shown in FIGS. 1–4, however, with a prism lens cross-sectional shape.
FIG. 12 is a transverse cross-sectional view of another embodiment of an intracorneal ring similar to the embodiment shown in FIGS. 1–4, however, with a prism lens cross-sectional shape.
FIG. 13 is a transverse cross-sectional view of another embodiment of an intracorneal ring similar to the embodiment shown in FIGS. 1–4, however, with a concave lens cross-sectional shape.
FIG. 14 is a transverse cross-sectional view of another embodiment of an intracorneal ring similar to the embodiment shown in FIGS. 1–4, however, with a plate type biconcave lens cross-sectional shape.

The intracorneal ring according to the present invention can be made from a variety of suitable biocompatible materials including polymethyl methacrylate (PMMA), silicone, hydrogel, collagen-based material (e.g. COLLAMER manufactured by STAAR Surgical A.G. of Switzerland), and other suitable materials. The collagen-based materials disclosed in U.S. Pat. Nos. 5,654,349, 5,654,363, 5,654,388, and 5,661,218 to Feingold et al., incorporated herein by reference, are particularly suitable for making intracorneal rings according to the present invention.

The intracorneal ring according to the present invention in some embodiments is made of material(s) and/or configured so that the intracorneal ring can be changed in shape and/or size in situ by applying one or more types of electromagnetic radiation to the implanted intracorneal ring. Thus, the conformation of the intracorneal ring can be adjusted or fine tuned to improve vision to the fullest extent. For example, the intracorneal ring can be adjusted in situ immediately after surgery, minutes after surgery, hours after surgery, days after surgery, months after surgery, and possibly years after surgery to compensate for changes to the eye (e.g. by aging).

Various suitable biomaterials such as hydrogels and collagen-based materials having high water content, for example, can be treated with an external laser to change the conformation of this material. For example, these materials can be possibly formulated to decrease in size (e.g. by causing a loss in water contact and/or by causing polymer chains to further cross-link and tighten and decrease dimensionally) after treatment with a laser, or possibly increase in size (e.g. by causing polymers chains in the material to relax and expand dimensionally). The change in shape can be equal along all three dimensional axes (i.e. isotropic), or can be unequal along one, two or three dimensional axes. The intracorneal ring can be treated with electromagnetic radiation in situ thereby causing localized deformation of one or more portions of the intracorneal ring, or can be treated to cause uniform overall deformation of the intracorneal ring.

The intracorneal ring according to the present invention can be made of a substantially rigid material (e.g. PMMA) or can be made of deformable material. The intracorneal ring can be configured to be substantially rigid, or can be configured to be deformable (e.g. foldable, rolled, compressible, etc.).

The intracorneal ring according to the present invention can be configured in shape and/or composed (e.g. differences in index of refraction with eye tissue) to function as a lens. Alternatively, the intracorneal ring can be configured and/or composed to provide no lens function. The function of the lens can be custom tailored to correct various conditions of the eye (e.g. astigmatism, presperiopia, etc.)

An intracorneal ring according to the present invention is shown in FIGS. 1–4. The intracorneal ring is preferably made of collagen-based material (e.g. COLLAMER), which is highly biocompatible. The thickness of the ring (FIGS. 4–6) can be selected and manufactured according to a prescription based on the examined patient to adjust the amount of correction of diopter to be created by the intracorneal ring, for example, a thicker ring may provide a greater amount of change of diopter. Alternatively, the change of thickness and so to diopter can be adjusted in situ by applying electromagnetic radiation (e.g. laser) to correct or further correction patient vision.

The intracorneal ring according to the present invention can have various configurations to provide a lens function of the intracorneal ring. Various transverse cross-sectional profiles provide for various lens corrections of the eye. In FIGS. 7, 8, 11 and 12, the transverse cross-sectional profiles define a prism shape in FIGS. 9, 10, 13, 14, 15 the transverse cross-sectional profiles define various combinations of concave and/or convex surfaces.

Figures 15, 16, 17, 18:
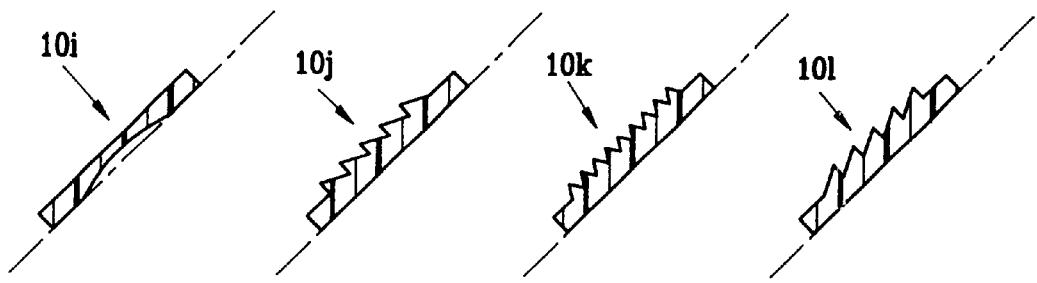
FIG. 15 is a transverse cross-sectional view of another embodiment of an intracorneal ring similar to the embodiment shown in FIGS. 1–4, however, with a concave lens cross-sectional shape.
FIG. 16 is a transverse cross-sectional view of another embodiment of an intracorneal ring similar to the embodiment shown in FIGS. 1–4, however, with a light interference gradient lens cross-sectional shape.
FIG. 17 is a transverse cross-sectional view of another embodiment of an intracorneal ring similar to the embodiment shown in FIGS. 1–4, however, with a multi-focal lens cross-sectional shape.
FIG. 18 is a transverse cross-sectional view of another embodiment of an intracorneal ring similar to the embodiment shown in FIGS. 1–4, however, with a multi-focal lens cross-sectional shape.

In FIG. 16, an aspect of the transverse cross-sectional profile is selected to provide a light gradient and/or light filtering effect. In FIGS. 17 and 18, an aspect of the transverse cross-sectional profile is configured to provide a lens having multi-focal properties. Any profile of the lens, for example, longitudinal or transverse cross-sectional, or any portion thereof, can remain constant in shape and/or size, or can vary contiguously or discretely along portions of the intracorneal ring to provide various lens effects.

Figures 19, 20:
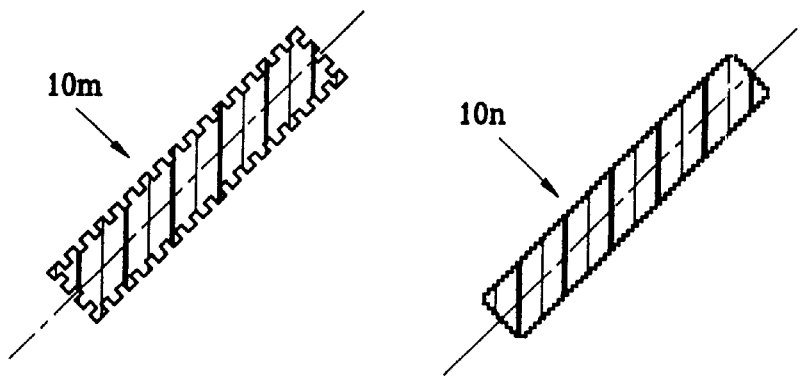
FIG. 19 is a transverse cross-sectional view of another embodiment of an intracorneal ring similar to the embodiment shown in FIGS. 1–4, however, provided with a surface texturing to facilitate tissue adhesion.
FIG. 20 is a transverse cross-sectional view of another embodiment of an intracorneal ring similar to the embodiment shown in FIGS. 1–4, however, provided with a surface texturing to increase frictional engagement with tissue.

In FIG. 19, the intracorneal 10 m ring is provided with a surface texturing of a type to enhance cell growth and adhesion to the surface of the intracorneal ring. In FIG. 20, the intracorneal ring 10n is provided with a surface texturing of a type to increase frictional contact with surrounding tissue. These texturing can be selected to prevent intracorneal ring rotation, enhance fixation, provide frosting (i.e. optical effect to, for example, prevent glare, provide coloring (e.g. to match iris color), provide texturing pattern (e.g. to match iris texturing pattern), etc.

Another embodiment of an intracorneal ring 20 according to the present invention is shown in FIG. 21. The intracorneal ring 20 is provided with multiple side-by-side full thickness opens side ports 22 around the circumference of the intracorneal ring 20 defining a plurality of bridging elements 24 connecting an upper edge portion 26 of the intracorneal ring 20 to a lower edge portion 28 of the intracorneal ring 20.

All or some of the bridging elements 24 can be treated with electromagnetic radiation (e.g. laser) in situ to expand or condense the height of the intracorneal ring 20. These changes in height will possibly cause changes in the thickness and/or band strength of the intracorneal rings depending on design and material to cause various effects to the eye (e.g. change of diopter, change of axis for astigmatism correction).

A further embodiment of an intracorneal ring 30 according to the present invention is shown in FIGS. 22 and 23. In this embodiment, the intracorneal ring 30 is composed of multiple layers or rings 30a, 30b, 30c, 30d, 30e and 30f. The rings 30a–f can be made of the same material or different materials from layer to layer. Some layers can be made to be treated with electromagnetic radiation in situ to change shape and/or size, and other layers can be made not react to electromagnetic radiation to create various lens shaping effects.

An even further embodiment of an intracorneal ring 40 according to the present invention is shown in FIGS. 24 and 25. In this embodiment, the intracorneal ring is provided with a ring portion 42 and haptic portions 44 and 46. The haptic portions 44 and 46 provide added fixation within the eye, and provide structural stability (e.g. prevents ring expansion or compression) to the intracorneal ring 40 and positioning stability within the eye (e.g. haptic portions 44 and 46 function as anchoring portions with surrounding tissue and prevent twisting of ring).

Figure 26:
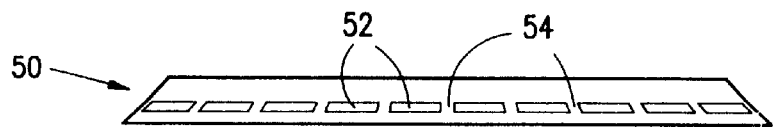
FIG. 26 is a side elevational view of another embodiment of an intracorneal ring according to the present invention configured to be adjustable in height in situ.

In FIG. 26, the intracorneal ring 50 is provided with a plurality of rectangle-shaped horizontally oriented open full thickness side ports 52 defining bridging elements 54. The height of the intracorneal ring 50 can be adjusted in situ with electromagnetic radiation (e.g. laser).

Figure 27:
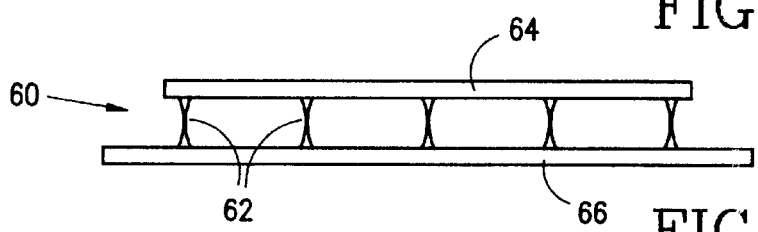
FIG. 27 is a side elevational view of another embodiment of an intracorneal ring according to the present invention configured to be adjustable in height in situ.

In FIG. 27, the intracorneal ring 60 is provided with a plurality of bridging elements 62 connecting an upper ring portion 64 to a lower ring portion 66. The height of the intracorneal ring 60 can be adjusted in situ with electromagnetic radiation (e.g. laser).

Figure 28:
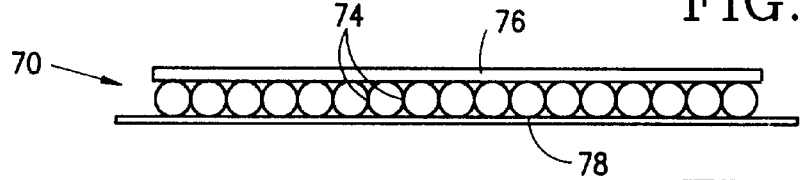
FIG. 28 is a side elevational view of another embodiment of an intracorneal ring according to the present invention configured to be adjustable in height in situ.

In FIG. 28, the intracorneal ring 70 is provided with a plurality of bridging rings 72 connecting an upper ring portion 74 to a lower ring portion 76. The height of the intracorneal ring 70 can be adjusted in situ with electromagnetic radiation (e.g. laser).

Figure 29:
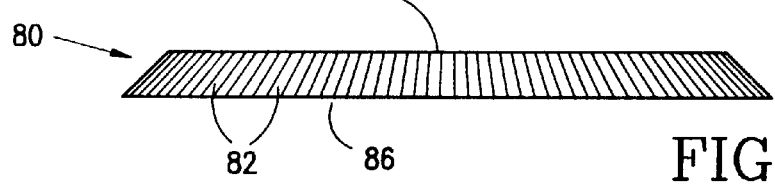
FIG. 29 is a side elevational view of another embodiment of an intracorneal ring according to the present invention configured to be adjustable in height in situ.

In FIG. 29, the intracorneal ring 80 is provided with multiple side-by-side ribs 82 connecting an upper edge portion 84 with a lower edge portion 86. The height of the intracorneal ring 80 can be adjusted in situ with electromagnetic radiation (e.g. laser).

Figure 30:
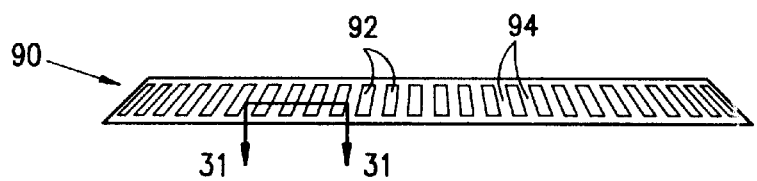
FIG. 30 is a side elevational view of another embodiment of an intracorneal ring according to the present invention configured to be adjustable in height in situ.
Figure 31:
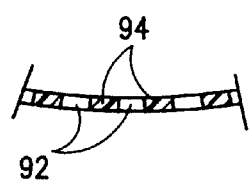
FIG. 31 is a partial broken away horizontally oriented cross-sectional view of the intracorneal ring, as indicated in FIG. 30, having open full thickness side ports.

In FIG. 30, the intracorneal ring 90 is provided with multiple rectangular-shaped vertically oriented open full thickness side ports 92 defining bridging elements 94. The height of the intracorneal ring 90 can be adjusted in situ with electromagnetic radiation (e.g. laser).

Figure 32:
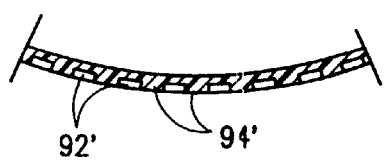
FIG. 32 is a partial broken away horizontally oriented cross-sectional view of the intracorneal ring having closed partial thickness side ports.

Alternatively, the side ports 92' can be closed and partial thickness, as shown in the modified embodiment in FIG. 32.

Figure 33:
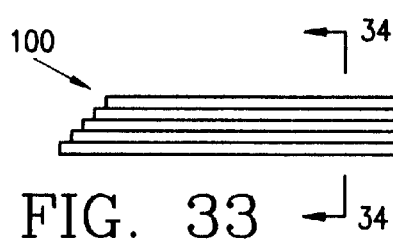
FIG. 33 is a side elevational view of another embodiment of an intracorneal ring according to the present invention configured to be adjustable in thickness in height in situ.
Figure 34:
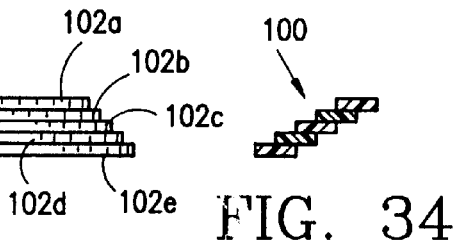
FIG. 34 is a transverse cross-sectional view of the intracorneal ring, as indicated in FIG. 33.
Figure 41:
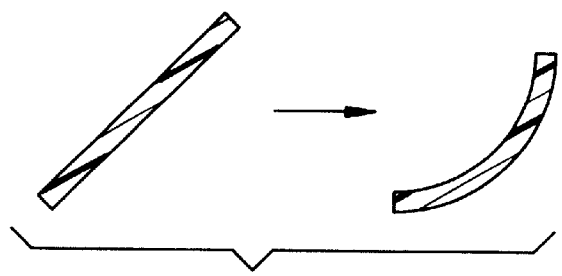
FIG. 41 is a transverse cross-sectional view of an intracorneal ring according to the present invention configured to change shape and thickness in situ.
Figure 42:
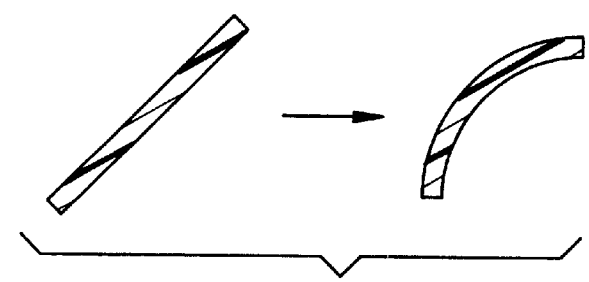
FIG. 42 is a transverse cross-sectional view of an intracorneal ring according to the present invention configured to change shape and thickness in situ.
Figure 43:
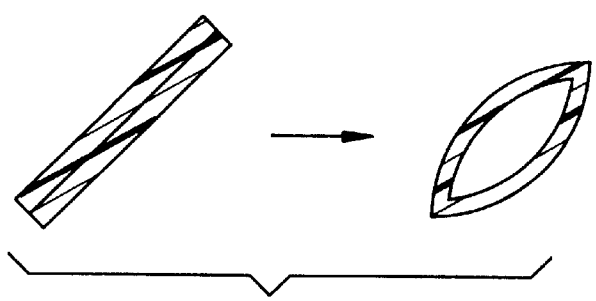
FIG. 43 is a transverse cross-sectional view of an intracorneal ring according to the present invention configured to change shape and thickness in situ.
Figure 44:
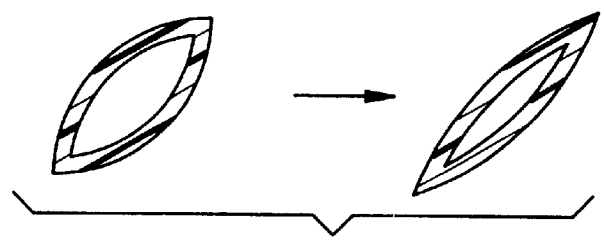
FIG. 44 is a transverse cross-sectional view of an intracorneal ring according to the present invention configured to change shape and thickness in situ.
Figure 45:
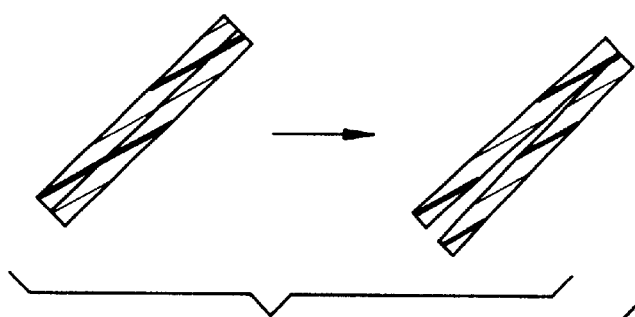
FIG. 45 is a transverse cross-sectional view of an intracorneal ring according to the present invention configured to change shape and thickness in situ.
Figure 46:
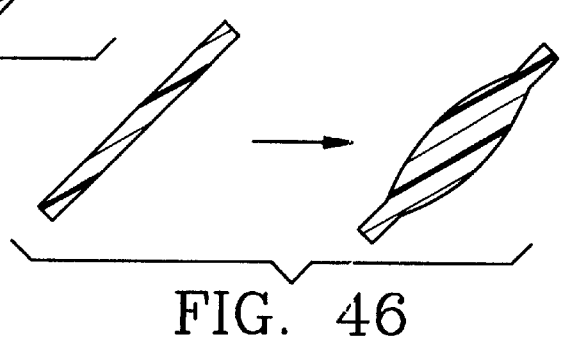
FIG. 46 is a transverse cross-sectional view of an intracorneal ring according to the present invention configured to change shape and thickness in situ.
Figure 47:
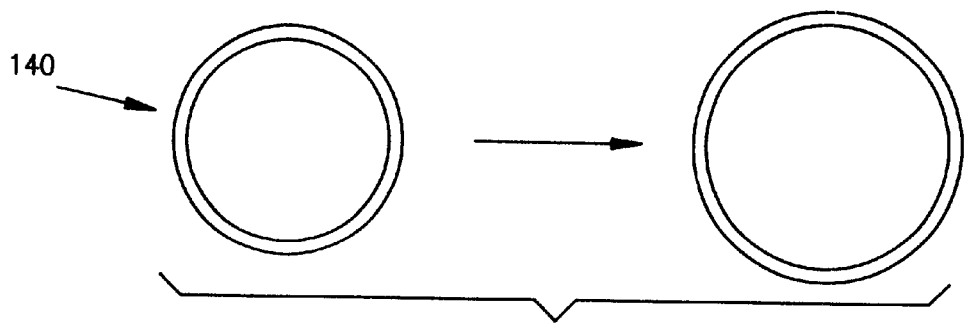
FIG. 47 is a diagrammatic top planar view of an intracorneal ring according to the present invention configured to increase in diameter in situ.
Figure 48:
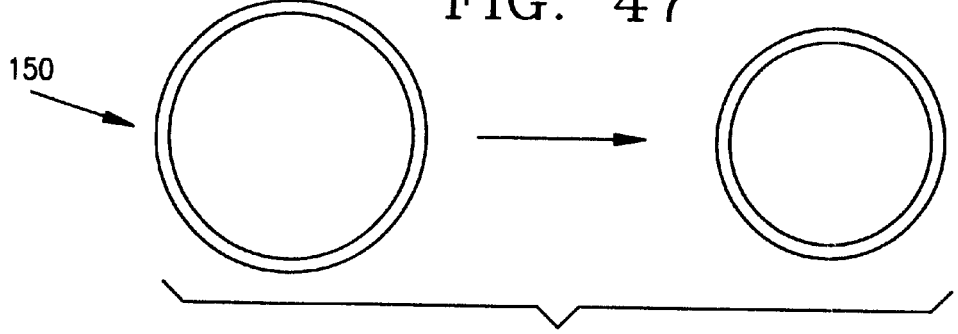
FIG. 48 is a diagrammatic top planar view of an intracorneal ring according to the present invention configured to increase in diameter in situ.
Figure 49:
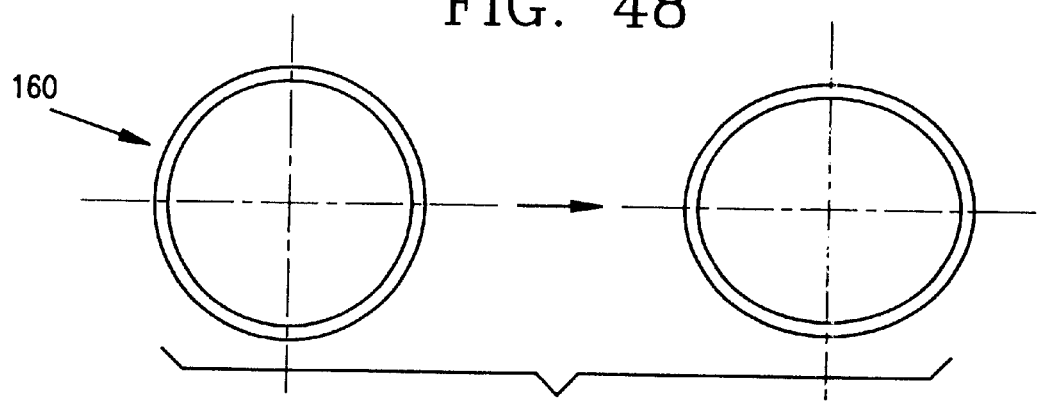
FIG. 49 is a diagrammatic top planar view of an intracorneal ring according to the present invention configured to change from circular to oval in situ.
Figure 50:
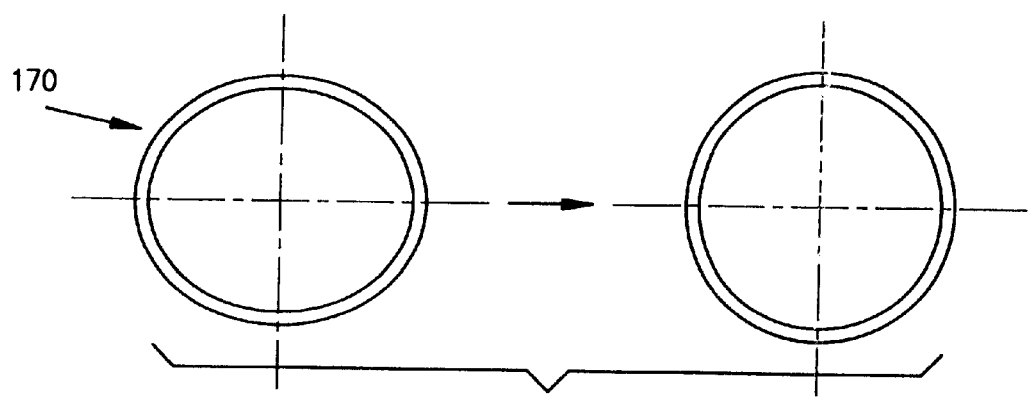
FIG. 50 is a diagrammatic top planar view of an intracorneal ring according to the present invention configured to change from oval to circular in situ.

In FIGS. 33 and 34, the intracorneal ring 100 is made of multiple vertically stacked rings 102a–e. The rings 102a–e can be made of the same or different materials. The height of the intracorneal ring 100 can be adjusted in situ with electromagnetic radiation (e.g. laser).

In FIG. 35 and 36, the intracorneal ring 110 is provided with a plurality of internal notches 112. One or more notches 112 can be treated with electromagnetic radiation in situ to cause the overall shape and/or thickness of the intracorneal ring to be changed.

In FIG. 37 and 38, the intracorneal ring 120 is provided with a plurality of slits 122 defining a plurality of ring portions 124 that can be adjusted in orientation independent of adjacent ring portions 124. The ring portions 124 are all connected to a separate continuous ring 126 providing a base ring support structure. The ring 126 can be made of the same material or a different material. For example, the ring 126 is made of a stronger material (e.g. polyacrylamide, polyethylene (e.g. Proline)) relative to the ring portions 124 (e.g. silicone, hydrogel)

In the embodiment shown in FIG. 39, the intracorneal ring 130 is made of four (4) connected rings 132a–d having tapering diameters. The rings 132a–d are provided with internal rings 134a–d made of the same or different material.

In FIGS. 41–46, the various embodiments are configured in transverse cross-section profiles to change profile shape and/or size in situ when treated with electromagnetic radiation (e.g. laser).

In FIGS. 47–50, the various embodiments are configured to change overall shape and/or size in situ when treated with electromagnetic radiation (e.g. laser).

Figure 51:
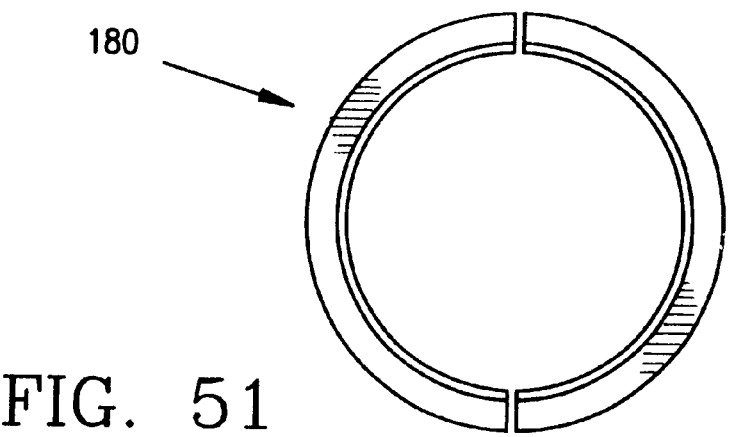
FIG. 51 is a top planar view of an intracorneal ring according to the present invention configured in two (2) circular segments.
Figure 52:
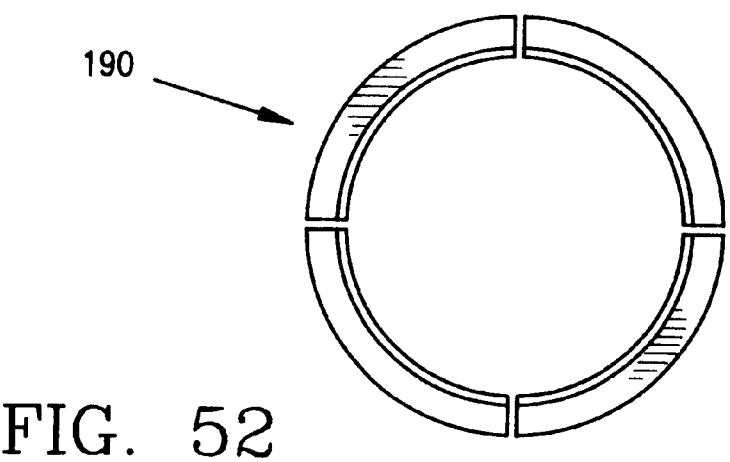
FIG. 52 is a top planar view of an intracorneal ring according to the present invention configured in four (4) circular segments.
Figure 53:
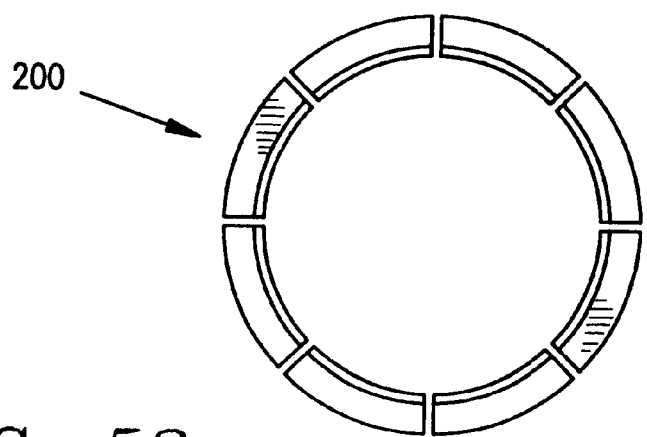
FIG. 53 is a top planar view of an intracorneal ring according to the present invention configured into eight (8) segments.

The intracorneal rings according to the present invention can be continuous (e.g. endless type) rings, or can be made up of separate ring sections, as shown in the embodiments of FIGS. 51–53.

METHODS

The intracorneal ring is implanted in the cornea of an eye, as shown in FIGS. 54 and 55.

The intracorneal ring can have sufficient rigidity and/or may be configured to surgically cut into the corneal tissue with an instrument for guiding movement of the intracorneal ring.

More preferably, a circular tunnel is provided beneath the surface of the cornea with a surgical instrument (e.g. treefind), or with a laser. A small incision is made from the surface of the cornea to the circular tunnel to provide a pathway for subsequent insertion of the intracorneal ring.

After implantation of the intracorneal ring, the intracorneal ring can be treated in situ with electromagnetic radiation (e.g.) to adjust the size and/or shape of the intracorneal ring.

We claim:

1. A method of implanting an intraocular implant configured to correct vision of an eye, comprising the steps of:

providing an intraocular implant configured and made of at least one material selected to undergo a substantially permanent change in conformation upon being subjected to electromagnetic radiation to change the intraocular implant from one configuration to another configuration;

implanting into the eye said intraocular implant configured to be substantially permanently changed from one configuration to another configuration upon subjecting said at least one material of said intraocular implant to the electromagnetic radiation to correct the vision of the eye; and treating said at least one material of said intraocular implant in situ with electromagnetic radiation to substantially permanently change said intraocular implant from the one configuration to another configuration to correct the vison of the eye.

2. A method according to claim 1, wherein a size of said intraocular implant is substantially permanently changed in situ.

3. A method according to claim 2, wherein a shape of said intraocular implant is substantially permanently changed in situ.

4. A method according to claim 1, wherein a shape of said intraocular implant is substantially permanently changed in situ.

5. A method according to claim 1, wherein said intraocular implant is configured to be adjustable from the one configuration to the other configuration to correct for astigmatism of the eye.

6. A method according to claim 1, wherein said intraocular implant is configured to function as a lens within the eye.

7. A method according to claim 1, wherein said intraocular implant is configured to change the power of the eye.

8. A method according to claim 1, wherein said intraocular implant is configured to be adjustable in thickness within the eye.

9. A method according to claim 1, wherein said intraocular implant is made from at least one material selected from the group consisting of polymethyl methacrylate, silicone polymer, acrylic, hydrogel, collagen-based polymer, and collagen containing polymer.

10. A method according to claim 1, wherein said intraocular implant includes at least one selected from the group consisting of an intraocular lens, deformable intraocular lens, phakic refractive lens, deformable phakic refractive lens, toric phakic correction lens intraocular ring, and intracorneal ring.

11. A method according to claim 1, including the step of further substantially permanently changing the configuration of the intraocular implant upon further subjecting the at least one material of the intraocular implant with additional electromagnetic radiation.

12. A method according to claim 1, wherein the electromagnetic radiation is applied to the intraocular implant from outside of the eye.

13. A method according to claim 1, wherein said at least one material of said intraocular implant is treated with electromagnetic radiation to adjust the visual correction of the eye.

14. A method according to claim 1, wherein said electromagnetic radiation is at least one selected from the group consisting of light, heat, ultra violet, laser and X-ray.

* * * * *